US00PP08110P

United States Patent [19]

Dehan

[11] Patent Number: Plant 8,110

[45] Date of Patent: Jan. 19, 1993

[54] IMPATIENS PLANT NAMED SAMBA

[75] Inventor: Klara Dehan, Holon, Israel

[73] Assignee: Danziger - "Dan" Flower Farm, Post Beit Dagan, Israel

[21] Appl. No.: 730,609

[22] Filed: Jul. 16, 1991

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Foley & Lardner

[57] ABSTRACT

A new cultivar of Impatiens plant named Samba, characterized by its large, red-purple flowers, medium tall plant height, dark green foliage, purple flower stems, and excellent branching.

1 Drawing Sheet

The present invention relates to a new and distinctive cultivar of New Guinea Impatiens plants, botanically known as Impatiens, and known by the cultivar name Samba. Samba was developed by me through controlled breeding by crossing a cultivar identified by the breeding number 0-17-A as the seed parent with the cultivar identified by number 0-4-G as the pollen parent.

Asexual reproduction of terminal or stem cuttings taken by the inventor at Mishmar Hashiva, Israel, has shown that the unique features of this new Impatiens are stabilized and are reproduced true to type in successive propagations.

The following characteristics distinguish the new impatiens from both its parent varieties and other cultivated impatiens of this type known and used in the floriculture industry:

1. Medium tall plant height.
2. Dark green foliage.
3. Very large red-purple flowers.
4. Unique flower shape.
5. The combination of flower color and shape is unique to New Guinea cultivars of this type.
6. Excellent branching.
7. Flower stems are purple.

The accompanying color photographs illustrate in the overall appearance and flower detail of this cultivar, showing the colors as true as it is reasonably possible to obtain in a colored reproduction of this type.

The top photo is a top view showing flowers and foliage of a portion of a plant.

The bottom photo is an enlarged showing of a single flower.

The following is a detailed description of my new Impatiens cultivar based on plants produced under commercial practice in Mishmar Hashiva, Israel. The description is based on observations and measurements made in the winter and early spring.

Color references are made to The Royal Horticultural Society Colour Chart except where general terms of ordinary dictionary significance are used.

Parentage: 0-17-A×0-4-G.

Propagation:

A. *Type cutting.*—Leaf cuttings with axillary buds and without flower buds.

B. *Time to initiate roots.*—8–10 days at 25°–30° C. summer and 20°–22° C. in winter.

C. *Rooting habit.*—Good.

Plant description:

A. *Form.*—Medium size mounded plant.

B. *Habit of growth.*—Vigorous with good branching; branching is spreading, making cultivar suitable for hanging pots.

C. *Foliage description.*—Medium large leaves, dark green in color. (1) Size: 9.5 cm in length and 3.5 cm in width. (2) Shape: Generally oval but elongated. (3) Margin: Finely serrated. (4) Color: Young foliage top side 137A; under side 146B. Mature foliage top side 137A; under side 138B. (5) Venation: Purple.

Flowering description:

A. *Flowering habits.*—Very floriferous; time from bud to open flower is approximately five days.

B. *Natural flowering season.*—Natural flowering season in moderate climates is in the spring. In Israel, flowering occurs also in the winter.

C. *Flower bud description.*—Normal.

D. *Flowers borne.*—Every branch has 6–7 buds in different stages. There are normally 3 flowers open at the same time on each branch.

E. *Quantity of flowers.*—Total inflorescence is approximately 30–35 flowers open at the same time for a period of 3–4 weeks, with flowering being continuous thereafter as long as temperatures remain above approximately 10° C. and there is at least a minimum level of light.

F. *Petals.*—(1) Shape: Two pairs heart shaped and a fifth petal non-heart shaped. (2) Color: Top side when opening is darker than 66A with no fading; underside 67A. (3) Number of petals: Five. (4) Size of flowers: Very large, 7 cm in diameter.

G. *Reproductive organs.*—(1) Stamens: One in number. (a) Anther color: White and purple. (b) Pollen color: White. (2) Pistils: (a) Stigma: Cone shaped, green in color. (b) Style: Green in color. (c) Ovaries: One in number, size 1.5 mm, light green in color.

I claim:

1. A new and distinct cultivar of Impatiens plant named Samba, as illustrated and described.

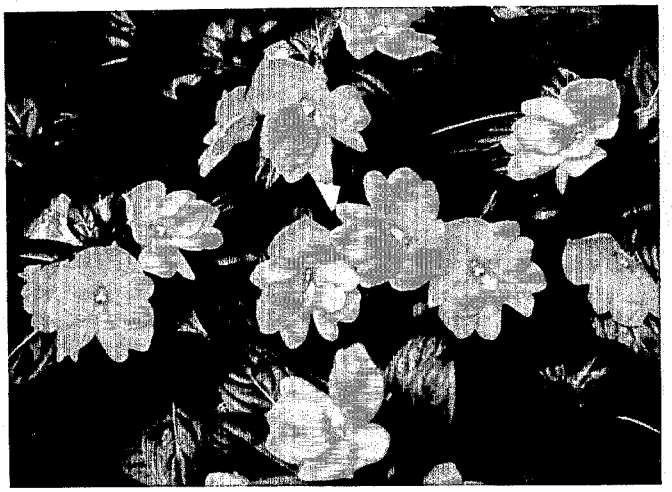
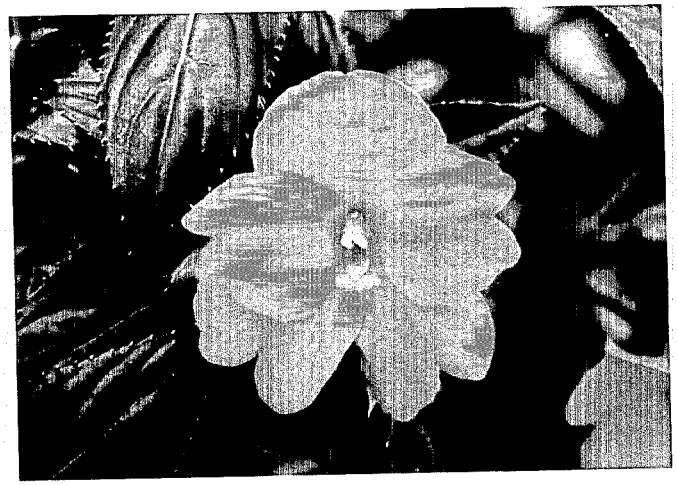

* * * * *